(12) United States Patent
He

(10) Patent No.: US 10,029,088 B2
(45) Date of Patent: Jul. 24, 2018

(54) BLOOD BAG STERILE CONNECTION METHOD AND DEVICE USED IN THE METHOD

(71) Applicant: Wuhan bms Medicaltech Co., Ltd, Hubei (CN)

(72) Inventor: Jun He, Guangdong (CN)

(73) Assignee: WUHAN BMS MEDICALTECH CO., LTD, Hubei (CN)

( * ) Notice: Subject to any disclaimer, the term of this patent is extended or adjusted under 35 U.S.C. 154(b) by 219 days.

(21) Appl. No.: 15/106,558

(22) PCT Filed: Dec. 18, 2014

(86) PCT No.: PCT/CN2014/094279
§ 371 (c)(1),
(2) Date: Jun. 20, 2016

(87) PCT Pub. No.: WO2015/090222
PCT Pub. Date: Jun. 25, 2015

(65) Prior Publication Data
US 2017/0028188 A1   Feb. 2, 2017

(30) Foreign Application Priority Data
Dec. 19, 2013  (CN) .......................... 2013 1 0701376

(51) Int. Cl.
*A61M 5/00* (2006.01)
*A61M 39/18* (2006.01)
(Continued)

(52) U.S. Cl.
CPC ................ *A61M 39/18* (2013.01); *A61J 1/10* (2013.01); *B29C 65/2038* (2013.01);
(Continued)

(58) Field of Classification Search
CPC ....... A61M 39/18; A61J 1/10; B29C 65/2038; B29C 66/1142; B29C 66/5221; B29C 66/857; B29L 2031/7148
See application file for complete search history.

(56) References Cited

U.S. PATENT DOCUMENTS

| 4,516,971 A | 5/1985 | Spencer |
| 4,832,773 A | 5/1989 | Shaposka et al. |
| 2008/0202669 A1 | 8/2008 | Zemmouri et al. |

FOREIGN PATENT DOCUMENTS

| CN | 1163823 | 11/1997 |
| CN | 1668449 | 9/2005 |

(Continued)

OTHER PUBLICATIONS

International Search Report (ISR) issued by World Intellectual Property Organization dated Mar. 13, 2015.
(Continued)

Primary Examiner — Philip R Wiest
(74) Attorney, Agent, or Firm — IP & T Group LLP

(57) ABSTRACT

A blood bag sterile connection method includes the following steps: 1) placing blood bag tubes above the wire box, clamping positions to be cut by using the vascular clamps, and simultaneously moving the two vascular clamps in opposite directions; 2) heating the composite metal wire, and cutting the blood bag tubes by using the composite metal wire; 3) after cutting the blood bag tubes, aligning the blood bag tubes to be connected; 4) moving the two vascular clamps towards each other, rolling away the used composite metal wire, and rolling out a new composite metal wire; 5) connecting the blood bag tubes by heating the composite metal wire, and simultaneously moving the two vascular clamps towards each other; and 6) returning the wire box to
(Continued)

the initial position, taking out the connected blood bag tubes, and returning the vascular clamps to the initial positions.

10 Claims, 4 Drawing Sheets

(51) Int. Cl.
    *B29C 65/20*     (2006.01)
    *B29C 65/00*     (2006.01)
    *A61J 1/10*     (2006.01)
    *B29L 31/00*     (2006.01)

(52) U.S. Cl.
    CPC ...... *B29C 65/2046* (2013.01); *B29C 66/1142* (2013.01); *B29C 66/5221* (2013.01); *B29C 66/857* (2013.01); *B29L 2031/7148* (2013.01)

(56) References Cited

FOREIGN PATENT DOCUMENTS

| | | |
|---|---|---|
| CN | 1668450 | 9/2005 |
| CN | 1798648 | 7/2006 |
| CN | 101076207 | 11/2007 |
| CN | 103767741 | 5/2014 |
| CN | 203662813 | 6/2014 |
| DE | 102007032771 | 1/2009 |
| EP | 0044204 | 1/1982 |
| EP | 0507321 | 10/1992 |
| JP | H0678971 | 3/1994 |
| JP | 2004-329223 | 11/2004 |
| TW | 522025 | 3/2003 |

OTHER PUBLICATIONS

Office Action issued by the State Intellectual Property Office dated May 5, 2015.

BLOOD BAG STERILE CONNECTION METHOD AND DEVICE USED IN THE METHOD

The present application is a national stage application of PCT/CN2014/094279 filed on Dec. 18, 2014, which claims the priority of Chinese Patent Application No. 201310701376.0, filed in Chinese Patent Office on Dec. 19, 2013, and entitled "BLOOD BAG STERILE CONNECTION METHOD AND DEVICE USED IN THE METHOD". The entire contents of each of the foregoing applications are herein incorporated by reference, and all related applications disclosed by the present application and quoted and incorporated in the present application are an indivisible part of the present application.

TECHNICAL FIELD

The present disclosure relates to the field of medical equipment, and in particular, to a blood bag sterile connection method and a device used in the method, and the method and the device are used for cutting and connecting blood bag tubes.

BACKGROUND

At present, traditional cutting blades are used for cutting and connecting blood bag tubes, the cutting mode of the cutting blades is realized easily, the cutting blades carry a lot of heat to easily fuse and connect the blood bag tubes, however, just because the cutting blades carry a lot of heat, in a connection process, the blood bag tubes generate chemical changes and are hot-melted together, the redundant heat of the cutting blades is actually waste of energy sources and if the blood bag tubes absorb excessive heat, the durations of the chemical changes will become overlong easily, which is not a reliable choice for clinical medicine.

Since a conventional connection device adopts the cutting blades, to connect the blood bag tubes, only if the conventional connection device is made to a certain volume, the heat carried by the cutting blades can be guaranteed to be enough to melt the blood bag tubes to connect the same, therefore, the volume of the conventional connection device is large, the utilization rate of a single cutting blade is very low, and the cutting material is seriously wasted.

When the conventional connection device is used for cutting and connecting the blood bag tubes, each cutting blade can only cut and connect the blood bag tubes once. The use demand of the conventional connection device on the cutting blade is very large. Only the part in contact with the blood bag tubes of each cutting blade is used, and the other parts are not used.

In summary, the cutting blades used by the conventional connection device are changed very frequently, and the actual utilization rate of each cutting blade is low, resulting in serious waste.

SUMMARY

In view of this, the present disclosure provides a blood bag sterile connection method and device, in which a composite metal wire is used for replacing a cutting blade to cut and connect blood bag tubes. The method is simple in steps and is convenient to realize, and the device not only has a simple structure, but also can solve the problem of large waste of the existing sterile connection device.

To realize the above purposes, the technical solution of the present disclosure is realized in the following manner:

On one aspect, the embodiment of the present disclosure provides a blood bag sterile connection method, including the following steps:

1) placing blood bag tubes above a wire box of a blood bag sterile connection device, clamping positions to be cut of the blood bag tubes by using vascular clamps, and simultaneously moving the two vascular clamps in opposite directions;

2) electrifying a composite metal wire of the blood bag sterile connection device for heating, and meanwhile, raising the wire box of the blood bag sterile connection device to cut the blood bag tubes by the composite metal wire of the wire box;

3) after the composite metal wire cuts the blood bag tubes, continuing to raise the wire box of the blood bag sterile connection device and retaining; meanwhile, aligning the blood bag tubes to be connected;

4) electrifying the composite metal wire of the blood bag sterile connection device for heating, meanwhile, moving the wire box of the blood bag sterile connection device downwards, and moving the two vascular clamps towards each other; rolling away the composite metal wire used during cutting under the action of a bobbin of the composite metal wire, and rolling out a new composite metal wire;

5) connecting the blood bag tubes via the composite metal wire, and simultaneously moving the two vascular clamps towards each other; and 6) returning the wire box of the blood bag sterile connection device to the initial position, opening the vascular clamps to take out the connected blood bag tubes, then clicking a reset key to return the vascular clamps to the initial positions, and thus completing the entire cutting and connecting process.

Further, in some embodiments, in the step 1), the two vascular clamps are simultaneously moved in opposite directions for 4-7 mm, in the step 3), the wire box of the blood bag sterile connection device continues to rise for 24 mm; in the step 4), the two vascular clamps are moved towards each other for 2-4 mm; and in the step 5), the two vascular clamps are moved towards each other for 2-3 mm.

Further, in some embodiments, in the step 2), the heating process of the composite metal wire is to quickly heat up to 300° C. within 2 seconds, and the time of the composite metal wire for cutting the blood bag tubes is 1-2 seconds.

Further, in some embodiments, the blood bag sterile connection device includes two power supplies, five motors, five motor drivers, a PLC controller, two vascular clamps, a wire box and a touch screen; wherein one power supply supplies power to the five motors, the five motor drivers, the PLC controller and the touch screen, and the other power supply is connected with the composite metal wire of the wire box for providing current to the metal wire; the first motor controls the horizontal movement of the first vascular clamp, the second motor controls the horizontal movement of the second vascular clamp, the third motor controls the rolling of a scroll of the wire box, the fourth motor controls the up and down movement of the wire box, and the fifth motor controls the back and forth movement of the second vascular clamp; the five motors are respectively connected with the PLC controller through the five motor drivers; and the PLC controller is connected with the touch screen.

Further, in some embodiments, the wire box includes a box body, a groove is formed in the upper part of the box body, and a chute is formed in the lower pan of the box body; a left scroll and a right scroll are arranged in the box body, and the composite metal wire on the left scroll is connected with the right scroll after passing through holes on both sides of the groove.

Further, in some embodiments, the box body includes a left box body and a right box body, which are connected by a buckle; the left scroll and the right scroll are arranged in the left box body; the hole is composed of a semicircular hole on the left box body and a semicircular hole on the right box body; and guide bars are arranged on both sides of the upper part of the left box body.

Compared with the prior art, the present disclosure has the following advantages:
1. the composite metal wire is used for cutting and connecting the blood bag tubes to solve the waste resulting from the fact that the existing sterile connection device adopts a cutting knife.
2. The method can be used for quickly connecting the blood bag tubes and can be used for realizing sterile connection.

On the other aspect, the embodiment of the present disclosure further provides a blood bag sterile connection device, including two power supplies, five motors, five motor drivers, a PLC controller, two vascular clamps, a wire box and a touch screen; wherein one power supply supplies power to the five motors, the five motor drivers, the PLC controller and the touch screen, and the other power supply is connected with a composite metal wire of the wire box for providing current to the metal wire; the first motor controls the horizontal movement of the first vascular clamp, the second motor controls the horizontal movement of the second vascular clamp, the third motor controls the rolling of a scroll of the wire box, the fourth motor controls the up and down movement of the wire box, and the fifth motor controls the back and forth movement of the second vascular clamp; the five motors are respectively connected with the PLC controller through the five motor drivers; and the PLC controller is connected with the touch screen.

Further, in some embodiments, the wire box includes a box body, a groove is formed in the upper part of the box body, and a chute is formed in the lower part of the box body; a left scroll and a right scroll are arranged in the box body, and the composite metal wire on the left scroll is connected with the right scroll after passing through holes on both sides of the groove.

Further, in some embodiments, the box body includes a left box body and a right box body, which are connected by a buckle; the left scroll and the right scroll are arranged in the left box body; the hole is composed of a semicircular hole on the left box body and a semicircular hole on the right box body; and guide bars are arranged on both sides of the upper part of the left box body.

Further, in some embodiments, the touch screen is connected with a remote server, and the touch screen is a 7-inch touch colored screen.

In the present disclosure, the blood bag tubes are cut and connected by the composite metal wire, the composite metal wire is placed in the wire box in rolls, the wire box is connected with the motors, the wire box can move up and down, the scrolls on the wire box can roll, the volume of the composite metal wire is very small, and the heat of the electrified composite metal wire is enough for cutting and connecting the blood bag tubes. Since the composite metal wire is used for replacing the cutting blade to cut and connect the blood bag tubes, a high material utilization rate can be guaranteed. In the present disclosure, a remote data transmission management system is added to guarantee the remote data transmission, state monitoring and service upgrade in the operation of the device, so that the operation reliability of the device is greatly improved.

In the present disclosure, the five motors are all step motors. One motor controls the up and down movement of the wire box for cutting and connecting; another one motor controls the rolling of the composite metal wire to change the new composite metal wire; the other three motors control the movement of the vascular clamps; and the actions of the five motors are automatically realized by the PLC controller.

The present disclosure further includes a PLC control system and a remote cloud service support system, internal components of the device are controlled by the PLC controller, the device data can be uploaded to a remote server through the touch screen, and meanwhile, reverse control can be realized by an instruction of the remote server.

In the present disclosure, the step motors are added to control the composite metal wire, and a man-machine interface and a remote data service cloud system better conforming to the trend development are added to greatly upgrade the functions of the existing sterile connection device, so that the problems of low use efficiency and waste of the traditional cutting blades are solved, the man-machine interface of the overall operation of the device is more advanced, the data processing of the device and the remote data processing are greatly improved, the operation efficiency of the device is improved, and meanwhile, the reliability of the maintenance efficiency is improved as well.

Compared with the prior art, the present disclosure has the following advantages:
1. the composite metal wire is used for cutting and connecting the blood bag tubes to solve the waste resulting from the fact that the existing sterile connection device adopts a cutting knife.
3. The device is small, simple in structure and convenient to use.
4. The PLC controller and the touch colored screen are used for improving the stability and the advancement of the device; and the efficiency is high.
5. The device can be used for quickly connecting the blood bag tubes and can be used for realizing sterile connection.
6. The method can be used for quickly connecting the blood bag tubes and can be used for realizing sterile connection.

BRIEF DESCRIPTION OF THE DRAWINGS

Accompany drawings constituting a part of the present disclosure are used for providing further understanding of the present disclosure, and schematic embodiments and illustration thereof of the present disclosure are used for explaining the present disclosure, and do not constitute improper limitation to the present disclosure.

In the accompany drawings.

In the figures: 1, box body; 1-1, left box body; 1-2, right box body; 2, chute; 3-1, left scroll; 3-2, right scroll; 4, composite metal wire; 5, groove; 6, guide bar; 7, touch screen; 8, wire box; 9, shell; 10, vascular clamp; 11, PLC controller; 12, motor; 13, motor driver; 14, guide rail; 15, power supply.

DETAILED DESCRIPTION OF THE PREFERRED EMBODIMENTS

Embodiments of the present invention will be further illustrated below in combination with the accompany drawings.

First Embodiment

Figure 1:
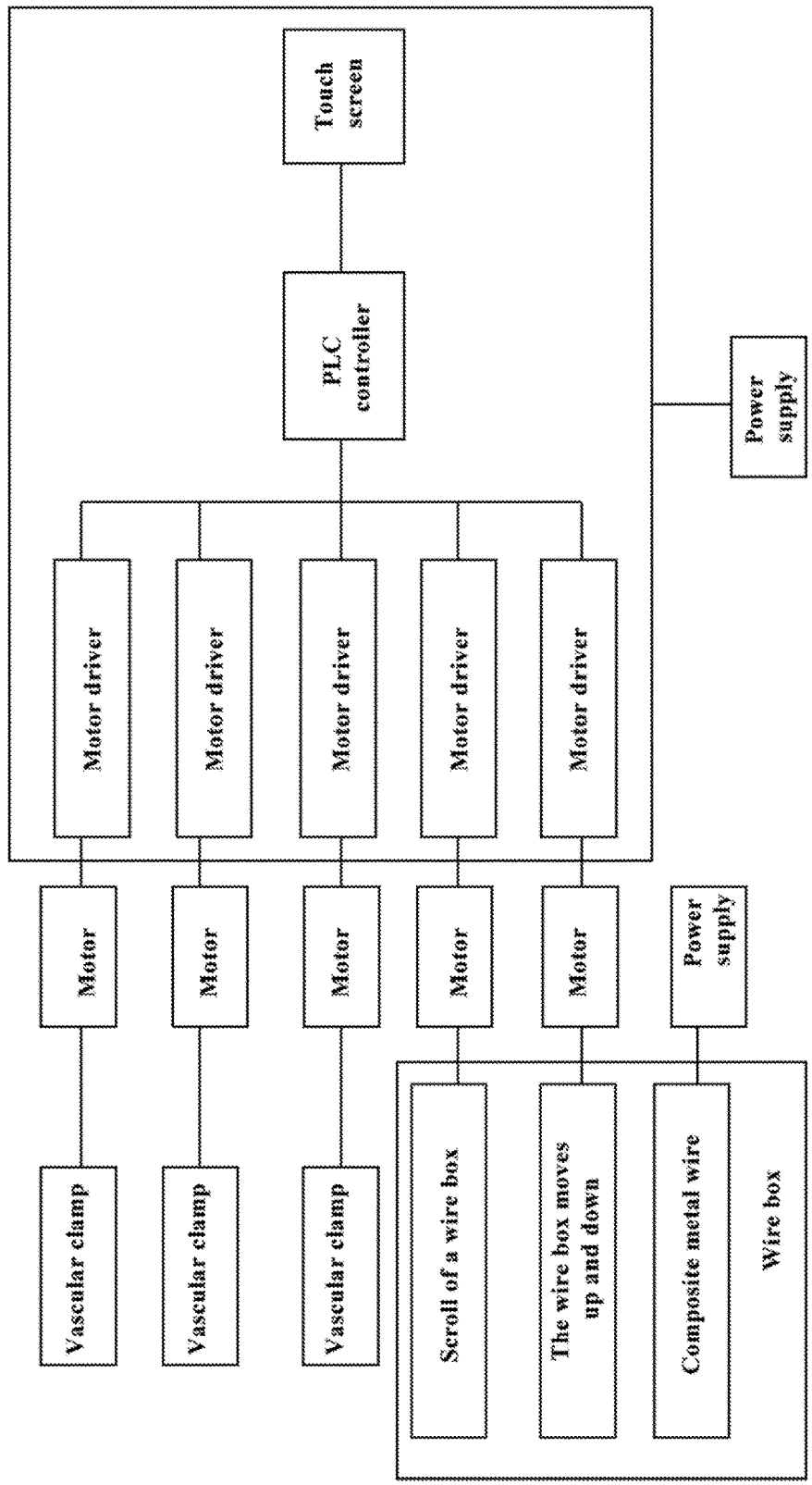
FIG. 1 is a structure block diagram of a sterile connection device.
Figure 2:
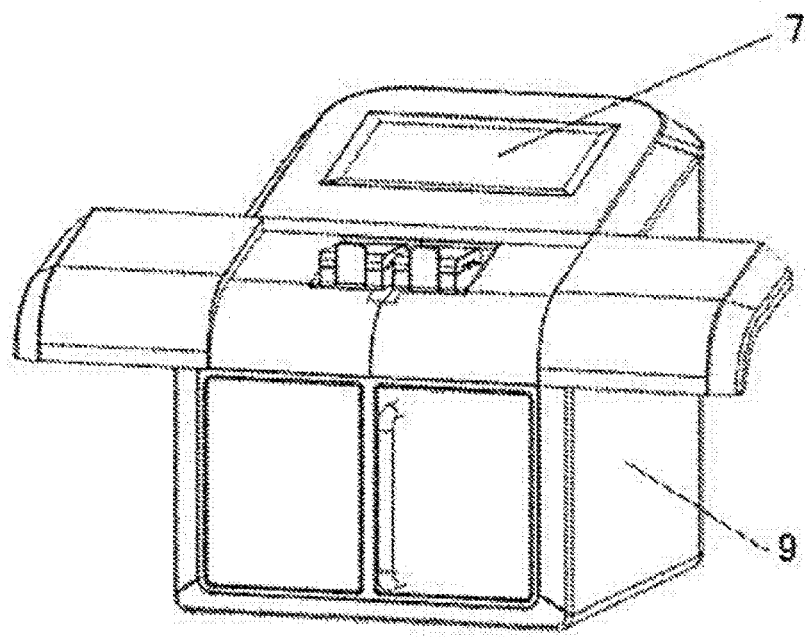
FIG. 2 is an overall external view of the sterile connection device.
Figure 3:
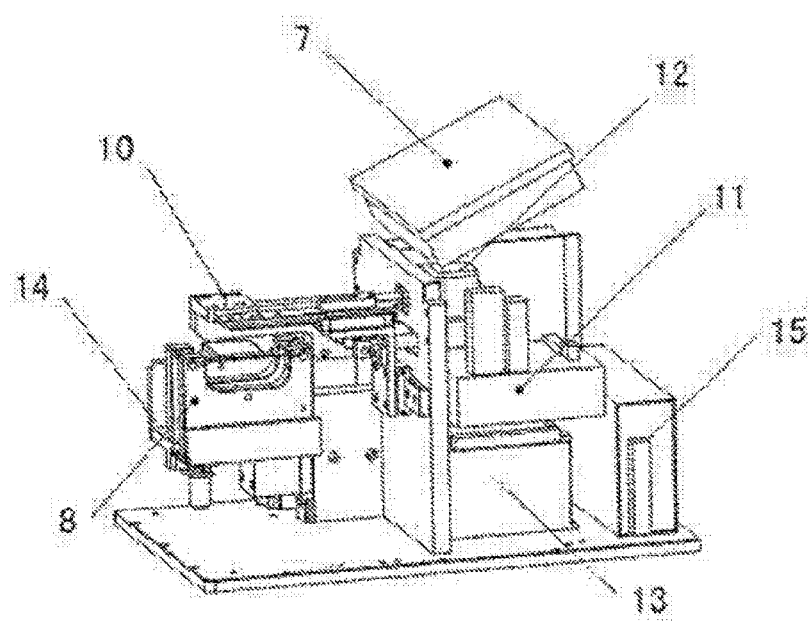
FIG. 3 is a schematic diagram of an inner structure of the sterile connection device.
Figure 4:
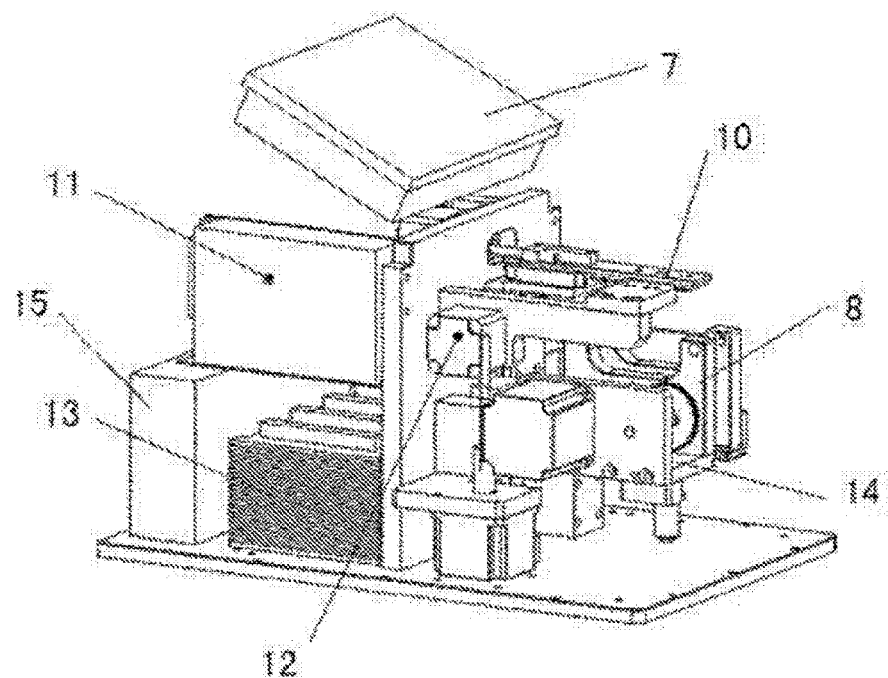
FIG. 4 is a schematic diagram of the inner structure of the sterile connection device.
Figure 5:
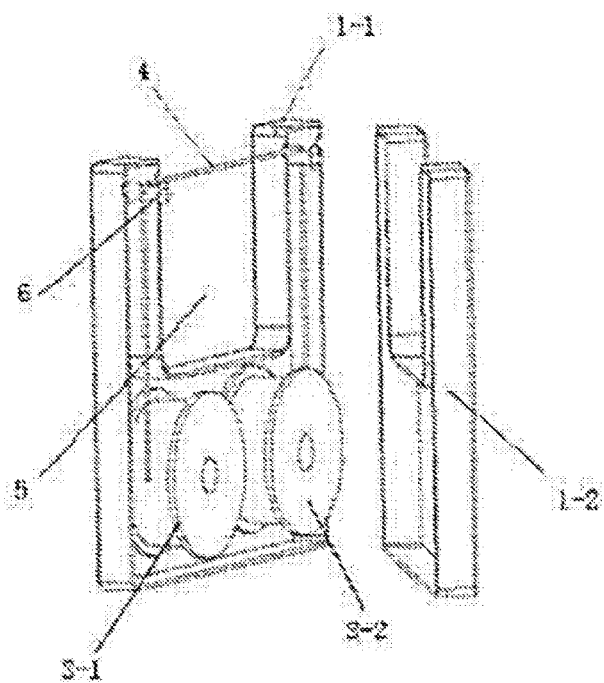
FIG. 5 is a schematic diagram of an inner structure of a wire box.
Figure 6:
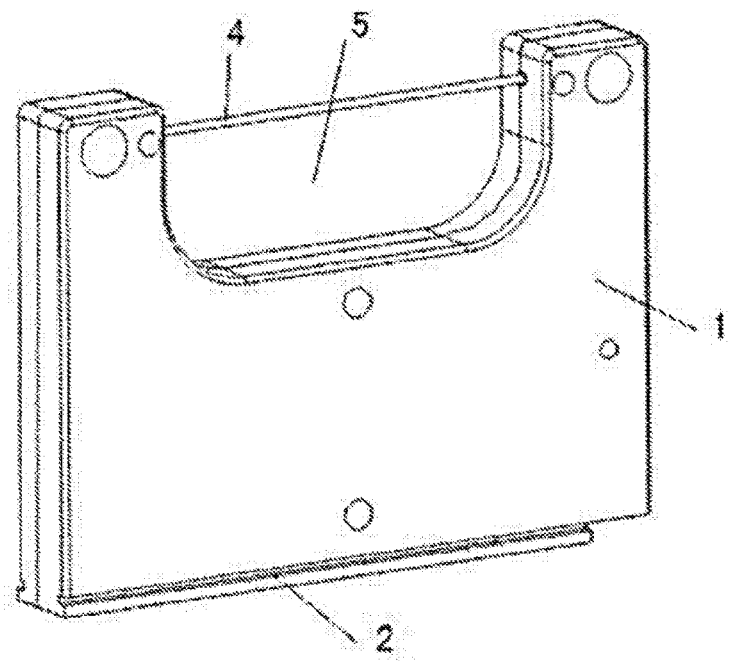
FIG. 6 is a schematic diagram of an overall structure of the wire box.
Figure 7:
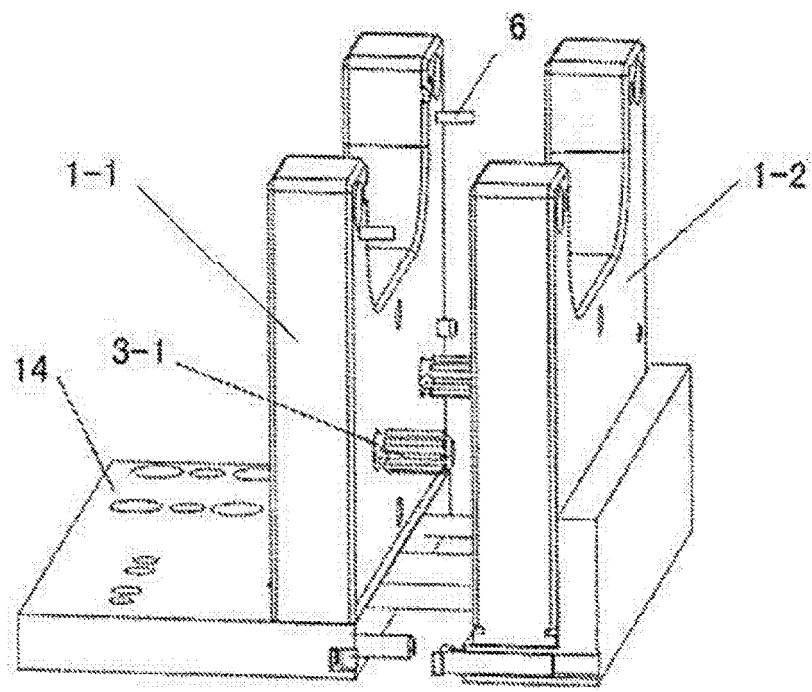
FIG. 7 is a schematic diagram of installation of the wire box.

As shown in FIG. 1 to FIG. 7, a blood bag sterile connection device, including two power supplies 15, five motors 12, five motor drivers 13, a PLC controller 11, two vascular clamps 10, a wire box 8 and a touch screen 7; wherein one power supply 15 supplies power to the five motors 12, the five motor drivers 13, the PLC controller 11 and the touch screen 7, and the other power supply 15 is connected with a composite metal wire 4 of the wire box 8 for providing current to the composite metal wire 4; the first motor 12 controls the horizontal movement of the first vascular clamp 10, the second motor 12 controls the horizontal movement of the second vascular clamp 10, the third motor 12 controls the rolling of a scroll of the wire box 8, the fourth motor 12 controls the up and down movement of the wire box 8, and the fifth motor 12 controls the back and forth movement of the second vascular clamp 10; the live motors 12 are respectively connected with the PLC controller 11 through the five motor drivers 13; and the PLC controller 11 is connected with the touch screen 7.

In the embodiment, the wire box 8 includes a box body 1, a groove 5 is formed in the upper part of the box body 1, and a chute 2 is formed in the lower part of the box body 1; a left scroll 3-1 and a right scroll 3-2 are arranged in the box body 1, and the composite metal wire 4 on the left scroll 3-1 is connected with the right scroll 3-2 after passing through holes on both sides of the groove 5.

In the embodiment, the box body 1 includes a left box body 1-1 and a right box body 1-2, which are connected by a buckle; the left scroll 3-1 and the right scroll 3-2 are arranged in the left box body 1-1; the hole is composed of a semicircular hole on the left box body 1-1 and a semicircular hole on the right box body 1-2; and guide bars 6 are arranged on both sides of the upper part of the left box body 1-1.

The connection mode of the embodiment is as follows: the touch screen 7 is installed on a shell 9 and is connected with the PLC controller 11 through a data line, the touch screen 7 sends an instruction, and the PLC controller 11 implements a specific operation to control the operation of the entire device; the motors 12 respectively control the horizontal movement of the two vascular clamps 10, the back and forth movement of one vascular clamp 10, the up and down movement of the wire box 8 and the rolling movement of the wire box 8 through guide rails 14 respectively; the wire box 8 is installed at the lower pan of the facade of the device, namely right below the two vascular clamps 10; each motor 12 needs to be provided with a motor driver 13, and the motor driver 13 is installed at the rear of the device; and the PLC controller 11 and the power supplies 15 are installed at the rear of the device.

When the wire box 8 is changed: the chute 2 at the lower part of the old box body 1 slips out from the guide rails 14 on the sterile connection device, and the wire box 8 in the sterile connection device to be changed slips to a specified position along the guide rails 14 on the sterile connection device. The current change and installation are completed.

Refer to FIG. 1 to FIG. 7, a blood bag sterile connection method using the blood bag sterile connection device includes the following steps:

1) placing blood bag tubes right above the wire box of the blood bag sterile connection device, clamping positions to be cut of the blood bag tubes by using the two vascular clamps, and simultaneously moving the two vascular clamps in opposite directions for 5 mm;

2) electrifying the composite metal wire 4 of the blood bag sterile connection device for heating, quickly heating up the composite metal wire to 300° C. within 2 seconds, and meanwhile, raising the wire box 8 of the blood bag sterile connection device to cut the blood bag tubes by the composite metal wire 4 of the wire box 8, wherein the cutting time is about 2 seconds;

3) after the composite metal wire 4 cuts the blood bag tubes, continuing to raise the wire box 8 of the blood bag sterile connection device for 3 mm and retaining; meanwhile, aligning the blood bag tubes to be connected;

4) electrifying the composite metal wire 4 of the blood bag sterile connection device for heating, meanwhile, moving the wire box 8 of the blood bag sterile connection device downwards, and moving the two vascular clamps 10 towards each other for 3 mm, rolling away the composite metal wire 4 used during cutting under the action of a bobbin of the composite metal wire 4, and rolling out a new composite metal wire 4;

5) connecting the blood bag tubes via the composite metal wire 4, and simultaneously moving the two vascular clamps towards each other for 2 mm, and 6) returning the wire box 8 of the blood bag sterile connection device to the initial position, opening the vascular clamps 10 to take out the connected blood bag tubes, then clicking a reset key to return the vascular clamps to the initial positions, and thus completing the entire cutting and connecting process.

Second Embodiment

The difference from the first embodiment lies in that: the touch screen 7 of the blood bag sterile connection device is a 7-inch touch colored screen, and the 7-inch touch colored screen is connected with a remote server for data transmission and control.

The difference from the first embodiment lies in that: in the step 1) of the blood bag sterile connection method, the two vascular clamps are simultaneously moved in opposite directions for 4 mm in the step 3), the wire box of the blood bag sterile connection device continues to rise for 2 mm; in the step 4), the two vascular clamps are moved towards each other for 4 mm; in the step 5), the two vascular clamps are moved towards each other for 3 mm; and in the step 2), the heating process of the composite metal wire is to quickly heat up to 300° C. within 2 seconds, and the time of the composite metal wire for cutting the blood bag tubes is 1 second.

In the step 3) of the embodiment, after the composite metal wire 4 cuts the blood bag tubes, the wire box 8 of the blood bag sterile connection device continues to rise for 2 mm and retains; and meanwhile, the second vascular clamp moves back and forth until the two blood bag tubes to be cut are aligned.

According to the present invention, the blood bag tubes are cut and connected by the composite metal wire 4, the composite metal wire 4 is placed in the wire box 8 in rolls, the wire box 8 is connected with the motors 12, the wire box 8 can move up and down, the scrolls on the wire box 8 can roll, the volume of the composite metal wire 4 is very small, and the heat of the electrified composite metal wire 4 is enough for cutting and connecting the blood bag tubes. Since the composite metal wire 4 is used for replacing the cutting blade to cut and connect the blood bag tubes, a high material utilization rate can be guaranteed. In the present invention, a remote data transmission management system is added to guarantee the remote data transmission, state monitoring and service upgrade in the operation of the device, so that the operation reliability of the device is greatly improved.

In the present invention, the five motors 12 are all step motors. One motor 12 controls the up and down movement and left and right movement of the wire box 8 for cutting and connecting; another one motor 12 controls the rolling of the composite metal wire 4 to change the new composite metal wire 4; the other three motors 12 control the movement of the vascular clamps 10; and the actions of the five motors are automatically realized by the PLC controller 11.

The present invention includes a PLC control system and a remote cloud service support system, internal components of the device are controlled by the PLC controller 11, the device data can be uploaded to a remote server through the touch screen 7, and meanwhile, reverse control can be realized by an instruction of the remote server.

In the present invention, the step motors are added to control the composite metal wire, and a man-machine interface and a remote data service cloud system better conforming to the trend development are added to greatly upgrade the functions of the existing sterile connection device, so that the problems of low use efficiency and waste of the traditional cutting blades are solved, the man-machine interface of the overall operation of the device is more advanced, the data processing of the device and the remote data processing are greatly improved, the operation efficiency of the device is improved, and meanwhile, the reliability of the maintenance efficiency is improved as well.

The above-mentioned embodiments are merely used for illustrating the technical solutions of the present invention, rather than limiting them, although the present invention has been described, in detail with reference to the preferred embodiments, those of ordinary skill in the art should understand that they could make modifications or equivalent substitutions to the technical solutions of the present invention without departing from the spirit or scope of the technical solutions of the present invention, and these modifications or equivalent substitutions shall fall into the scope of the claims of the present invention.

PRACTICABILITY

According to the blood bag sterile connection method and device provided by the embodiments of the present disclosure n which the composite metal wire is used for replacing the cutting blades to cut and connect the blood bag tubes, the method is simple in steps and is convenient to realize, and the device not only has a simple structure, but also can solve the problem of large waste of the existing sterile connection device. Therefore, the blood bag sterile connection method and the device used in the method provided by the embodiment's of the present disclosure have industrial applicability.

The invention claimed is:

1. A blood bag sterile connection method, comprising the following steps:
   1) placing blood bag tubes above a wire box of a blood bag sterile connection device, clamping positions to be cut of the blood bag tubes by using two vascular clamps, and simultaneously moving the two vascular clamps in opposite directions;
   2) electrifying a composite metal wire of the blood bag sterile connection device for heating, and meanwhile, raising the wire box of the blood bag sterile connection device to cut the blood bag tubes by the composite metal wire of the wire box;
   3) after the composite metal wire cuts the blood bag tubes, continuing to raise the wire box of the blood bag sterile connection device and retaining; meanwhile, aligning the blood bag tubes to be connected;
   4) electrifying the composite metal wire of the blood bag sterile connection device for heating, meanwhile, moving the wire box of the blood bag sterile connection device downwards, and moving the two vascular clamps towards each other; rolling away the composite metal wire used during cutting under the action of a bobbin of the composite metal wire, and rolling out a new composite metal wire;
   5) connecting the blood bag tubes via the composite metal wire, and simultaneously moving the two vascular clamps towards each other; and
   6) returning the wire box of the blood bag sterile connection device to the initial position, opening the vascular clamps to take out the connected blood bag tubes, then clicking a reset key to return the vascular clamps to the initial positions, and thus completing the entire cutting and connecting process.

2. The method of claim 1, wherein in the step 1), the two vascular clamps are simultaneously moved in opposite directions for 4-7 mm; in the step 3), the wire box of the blood bag sterile connection device continues to rise for 2-4 mm; in the step 4), the two vascular clamps are moved towards each other for 2-4 mm; and in the step 5), the two vascular clamps are moved towards each other for 2-3 mm.

3. The method of claim 1, wherein in the step 2), the heating process of the composite metal wire is to quickly heat up to 300° C. within 2 seconds, and the time of the composite metal wire for cutting the blood bag tubes is 1-2 seconds.

4. The method of claim 1, wherein the blood bag sterile connection device comprises two power supplies, five motors, five motor drivers, a PLC controller, two vascular clamps, a wire box and a touch screen; wherein one power supply supplies power to the five motors, the five motor drivers, the PLC controller and the touch screen, and the other power supply is connected with the composite metal wire of the wire box for providing current to the metal wire; the first motor controls the horizontal movement of the first vascular clamp, the second motor controls the horizontal movement of the second vascular clamp, the third motor controls the rolling of a scroll of the wire box, the fourth motor controls the up and down movement of the wire box, and the fifth motor controls the back and forth movement of the second vascular clamp; the five motors are respectively connected with the PLC controller through the five motor drivers; and the PLC controller is connected with the touch screen.

5. The method of claim 4, wherein the wire box comprises a box body, a groove is formed in the upper part of the box body, and a chute is formed in the lower part of the box body; a left scroll and a right scroll are arranged in the box body, and the composite metal wire on the left scroll is connected with the right scroll after passing through holes on both sides of the groove.

6. The method of claim 4, wherein the box body comprises a left box body and a right box body, which are connected by a buckle; the left scroll and the right scroll are arranged in the left box body; the hole is composed of a semicircular hole on the left box body and a semicircular hole on the right box body; and guide bars are arranged on both sides of the upper part of the left box body.

7. A blood bag sterile connection device used in the method of claim 1, comprising: two power supplies, five motors, five motor drivers, a PLC controller, two vascular clamps, a wire box and a touch screen; wherein one power supply supplies power to the five motors, the five motor drivers, the PLC controller and the touch screen, and the other power supply is connected with a composite metal wire of the wire box for providing current to the metal wire; the first motor controls the horizontal movement of the first vascular clamp, the second motor controls the horizontal movement of the second vascular clamp, the third motor controls the rolling of a scroll of the wire box, the fourth motor controls the up and down movement of the wire box, and the fifth motor controls the back and forth movement of the second vascular clamp; the five motors are respectively connected with the PLC controller through the five motor drivers; and the PLC controller is connected with the touch screen.

8. The device of claim 7, wherein the wire box comprises a box body, a groove is formed in the upper part of the box body, and a chute is formed in the lower part of the box body; a left scroll and a right scroll are arranged in the box body, and the composite metal wire on the left scroll is connected with the right scroll after passing through holes on both sides of the groove.

9. The device of claim 8, wherein the box body comprises a left box body and a right box body, which are connected by a buckle; the left scroll and the right scroll are arranged in the left box body; the hole is composed of a semicircular hole on the left box body and a semicircular hole on the right box body; and guide bars are arranged on both sides of the upper part of the left box body.

10. The device of claim 7, wherein the touch screen is connected with a remote server.

* * * * *